US005945285A

United States Patent [19]
Mekalanos et al.

[11] Patent Number: 5,945,285
[45] Date of Patent: Aug. 31, 1999

[54] ***VIBRIO CHOLERAE* HAVING INCREASED SENSITIVITY TO ANTIBIOTICS**

[75] Inventors: John J. Mekalanos, Cambridge; Matthew K. Waldor, Brookline, both of Mass.

[73] Assignee: President and Fellows of Harvard College, Cambridge, Mass.

[21] Appl. No.: 08/882,455

[22] Filed: Jun. 26, 1997

Related U.S. Application Data

[60] Provisional application No. 60/021,081, Jun. 27, 1996.

[51] Int. Cl.[6] .............................. C12Q 1/68; C12N 1/20; C07H 21/04

[52] U.S. Cl. .......................... 435/6; 435/252.3; 536/23.1; 536/23.7

[58] Field of Search .................. 435/6, 252.3; 536/23.1, 536/23.7

[56] References Cited

U.S. PATENT DOCUMENTS

| | | | |
|---|---|---|---|
| 4,882,278 | 11/1989 | Mekalanos | 435/477 |
| 4,968,619 | 11/1990 | Curtiss, III | 435/252.33 |
| 5,110,588 | 5/1992 | Morona et al. | 424/200.1 |

FOREIGN PATENT DOCUMENTS

| | | |
|---|---|---|
| WO 95/18633 | 7/1995 | WIPO . |

OTHER PUBLICATIONS

Pearson et al., "New Attenuated Derivatives of *Vibrio cholerae*" Res. Microbiol. 141:893–899 (1990).

Sinha et al., "A streptomycin–sensitive revertant of a streptomycin–dependent strain of *Vibrio cholerae*" Bull. World Health Organ. 53(4):482–484.

Ichinose et al., "The characterization of *Vibrio cholerae* isolated in Kenya in 1983" Journal of Tropical Medicine and Hygiene 89:269–276 (1986).

Coster et al., "Safety, immunogenicity and efficacy of a live attenuated *Vibrio cholerae* O139 vaccine protype, Bengal–15", Lancet 345:949–952 (1995).

Mekalanos, "Live bacterial vaccines: environmental aspects", Current Opinion in Biotechnology 5:312–319 (1994).

Mekalanos and Sadoff, "Cholera vaccines: fighting an ancient scourge", Science 265:1387–1389 (1994).

Mekalanos et al., "Live cholera vaccines: perspectives on their construction and safety", Bulletin de I'Institut Pasteur 93:255–262 (1995).

Tacket et al., "Initial clinical studies of CVD112 *Vibrio cholerae* O139 live oral vaccine: safety and efficacy against experimental challenge", J. Infect. Dis. 172:883–886 (1995).

Waldor and Mekalanos, "Emergence of a new cholera pandemic: molecular analysis of virulence determinants in *Vibrio cholerae* O139 and development of a live vaccine prototype", J. Infect. Dis. 170:278–283 91994).

Waldor and Mekalanos, "*Vibrio cholerae* O139 specific gene sequences", Lancet 343:1366 (1994).

*Primary Examiner*—David Guzo
*Assistant Examiner*—William Sandals
*Attorney, Agent, or Firm*—Clark & Elbing LLP; Kristina Bieker-Brady

[57] ABSTRACT

The invention provides bacterial strains with increased sensitivity to antibiotics and methods for making and using the strains.

12 Claims, 5 Drawing Sheets

VIBRIO CHOLERAE HAVING INCREASED SENSITIVITY TO ANTIBIOTICS

CROSS-REFERENCED APPLICATIONS

This application claims priority from U.S. application Ser. No. 60/021,081, filed on Jun. 27, 1996.

GOVERNMENT SPONSORED RESEARCH

This work was supported by Public Health Service Grants AI-18045, AI01321-01.

BACKGROUND OF THE INVENTION

The field of the invention is cholera vaccines.

Cholera is a severe and sometimes lethal diarrheal disease caused by the Gram-negative bacterium *Vibrio cholerae*. Historically only the O1 serogroup of *V. cholerae* has been associated with epidemic cholera. However, in early 1993 in India and Bangladesh, a major cholera epidemic was caused by a novel non-O1 serogroup of *V. cholerae* named *V. cholerae* O139. Strains belonging to this newly emerged *V. cholerae* serogroup replaced the endemic El Tor O1 strains of *V. cholerae* to become the principal clinical and environmental isolate of *V. cholerae* on the Indian subcontinent (Cholera Working Group, 1993, supra).

The initial microbiologic characterization of *V. cholerae* O139 revealed that this serogroup was closely related to the El Tor biotype of *V. cholerae* O1. The shared properties of *V. cholerae* O139 and El Tor O1 strains include (1) the agglutination of chicken red blood cells; (2) resistance to polymyxin B (Cholera Working Group, 1993, Lancet 342:387–390, 1993); (3) in vitro growth conditions for the expression of virulence factors (Waldor et al., Infect. Immun. 62:72–78, 1994); (4) identical sized restriction fragments for genes which have known polymorphisms (Calia et al., Infect. Immun. 62:1504–1506, 1994; Waldor et al., supra); (5) identical electrophoretic types by multilocus enzyme electrophoresis analysis (Popovic et al., J. Infect. Dis. 171:122–127, 1995); (6) tandem duplications of the CTX genetic element (Waldor et al., J. Infect. Dis. 170:278–283, 1994); and (7) identical chromosomal location of the CTX genetic element (Waldor et al., 1994, supra). These findings support the hypothesis that *V. cholerae* O139 is a derivative of an El Tor O1 strain of *V. cholerae*. DNA sequence analysis of tcpA, which encodes the major subunit of the toxin co-regulated pilus TCP in El Tor O1, classical O1, and O139 strains has given strong support to this hypothesis (Iredell et al., FEMS Microbiol. Lett. 121:47–54, 1994; Rhine et al., Mol. Microbiol. 13:1013–1020, 1994). While there is approximately 30% difference in the sequence of tcpA between classical and El Tor O1 strains, the O139 and El Tor tcpA sequences were identical (Rhine et al., supra). Recent analyses of the sequences of the gene encoding aspartate-semialdehyde dehydrogenase in various strains of *V. cholerae* also support a closer genetic relationship between O139 strains with El Tor O1 strains rather than with classical O1 strains.

While *V. cholerae* O139 shares many characteristics with the El Tor O1 strains that were endemic on the Indian subcontinent at the time *V. cholerae* O139 arose, O139 strains had two principal features which distinguished them from the El Tor O1 strains (Nair et al., J. Clin. Microbiol. 32:2775–2779, 1994). These features were the novel O139 serogroup antigen and a distinct set of antibiotic resistances. The gram-negative Bacteroides obligate anaerobe conjugative transposons range in size from 65 kb to 150 kb, generally encode resistance to tetracycline, and sometimes contain genes encoding resistance to erythromycin and clindamycin as well (Salyers et al., J. Bacteriol. 177:5727–5731, 1995). The conjugative transposons described in Gram-positive bacteria have similar properties but at least in the case of the Tn916–Tn1545 family, they do not exhibit a high degree of insertion site-specificity and excise from the donor strain independent of recA (Clewell et al., Trends Microbiol. 3:229–236, 1995). These Gram-positive conjugative transposons generally encode resistance to tetracycline as well other antibiotics (Clewell et al., supra). Previous studies have demonstrated that trimethoprim resistance genes in *V. cholerae* are plasmid- or transposon-encoded (Gerbaud et al., Ann. Inst. Pasteur/ Microbiol. 136B:265–273, 1985).

For individual safety and public health reasons, a safe cholera vaccine should be sensitive to as many commonly used antibodies as possible.

SUMMARY OF THE INVENTION

We have discovered a *v. cholerae* genomic element (the SXT element) which encodes resistance to at least four commonly used antibiotic drugs.

In the first aspect, the invention features genetically engineered cholera cell having sensitivity to an antibiotic selected from the group comprising sulfamethoxazole, trimethoprim, chloramphenicol, and streptomycin. The cell of the invention is derived from a parent cell resistant to the aforementioned antibiotic or antibiotics. In preferred embodiments, the cell is a Bengal O139 cell, the sensitivity is the result of a deletion, and the sensitivity is to at least two of the antibiotics selected from the group consisting of sulfamethoxazole, trimethoprim, chloramphenicol, and streptomycin.

Most preferably, the sensitivity is to all of the antibiotics selected from groups consisting of sulfamethoxazole, trimethoprim, chloramphenicol, and streptomycin, and the sensitivity is as a result of a deletion of at least a portion of the SXT element.

In another aspect, the invention features a method of making a bacterial cell resistant to at least one of the antibiotics selected from the group consisting of sulfamethoxazole, trimethoprim, chloramphenicol, and streptomycin sensitive to the antibiotic (or antibiotics). The method includes the steps of: a) taking a parental bacterial cell resistant to at least one of the antibiotics and having at least a portion of the SXT genetic element; b) mutating the SXT genetic element; and c) screening for the absence or alteration of at least a portion of the SXT genetic element or screening for sensitivity to at least one of the aforementioned antibiotics. A strain which has new sensitivity as a result of this method is also a strain of the invention.

In a preferred embodiment, the method further includes the step of making the strain recA⁻.

In another preferred embodiment, the parental bacterial cell is a *V. cholerae* cell, most preferably a non-O1 *V. cholerae* cell such as Bengal O139.

By "SXT element" is meant an approximately 62 kB transposable chromosomely integrating conjugative transposon-like element that encodes resistances to sulfamethoxazole, trimethoprim, chloramphenicol, and streptomycin. Preferably, the element is approximately 62 kB transposable chromosomely integrating conjugative transposon-like element.

Preferably, and SXT element is capable of moving from a *V. cholerae* cell to another cholerae cell. Most preferably, it is capable of moving from a *V. cholerae* cell to an *E. coli* cell.

By "bacterial cell" is meant any bacterial cell that contains the SXT element or an element which hybridizes to DNA encoding the SXT element under stringent conditions (See, e.g., protocol for enhanced chemiluminecense nucleic acid hybridization protocol, Amersham., PLC, UK (e.g., 43° with Amersham hybridization solution)).

By "deletion of SXT element" is meant any deletion which removes at least some of the SXT element nucleic acids and confers sensitivity to at least one of the following antibiotics: sulfamethoxazole, trimethoprim, chloramphenicol, and streptomycin. The preferred deletion has a reversion frequency of less than $10^{-18}$. Also preferred is a deletion which confers sensitivity to all four antibiotics. Also preferable is a deletion which prevents integration of an SXT element into the chromosomal DNA.

By "mutation" is meant any alteration in the nucleic acid sequence of SXT element, including insertions, deletions, and missense mutations. Preferred mutations confer sensitivity to at least one of the following antibiotics: sulfamethoxazole, trimethoprim, chloramphenicol, and streptomycin.

Figure 1:
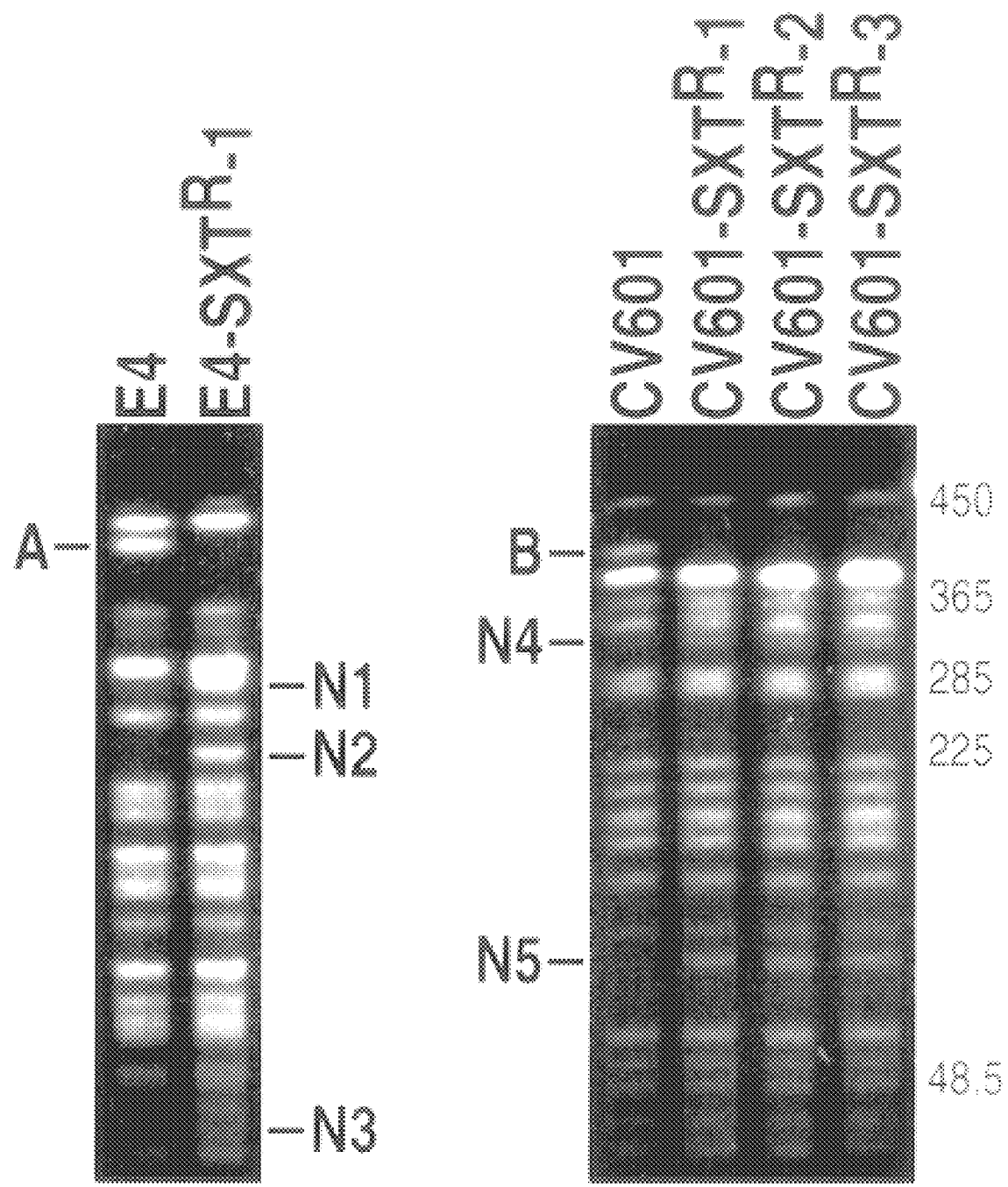
FIG. 1 shows pulse field gel electrophoresis analysis of a *V. cholerae* O1 recipient of the SXT element derived from the conjugation of MO10 with E4, (E4-$SXT^R$-1)(left), and three independently derived *E. coli* (strain CV601) recipients of the SXT element derived from the conjugation of E4-$SXT^R$-1 with CV601, (CV601-$SXT^R$-1), of O139 strain 5 MTB with CV601, (CV601-$SXT^R$-2), and MO10 with CV601, (CV601-$SXT^R$-3), (right). The missing fragment in the *V. cholerae* O1 and *E. coli* recipients of the SXT element are labelled A and B respectively. The novel bands in E4-$SXT^R$, are labeled N1, N2 and N3 and in the CV601-$SXT^R$ strains N4 and N5. Molecular weight markers in kb are shown on the left.

FIG. 2 shows southern blot analysis of independently derived *V. cholerae* O1 recipients of the SXT element derived from the conjugation of MO10×E4 (E4-$SXT^R$-1 and E4-$SXT^R$-2) and MO10×O395-NT (O395-NT-$SXT^R$-1 and O395-NT-$SXT^R$-2). The cosmid pSXT1 and the chromosomal DNA from the indicated strains were digested with PstI, electrophoresed, and analyzed by Southern blot hybridization using pSXT1 as a probe. The fragment labeled 'V' contains only vector DNA; the fragments labeled 'E' contain DNA only from the SXT element and the fragments labeled 'V+E' contain both vector and element DNA. The fragments labeled 'element jcn' (element junction) is entirely within the SXT element, with one PstI site located outside of the probe. The fragments labeled 'chrom. jcn.' (chromosome junction) are junctions of the SXT element with the chromosome. Molecular weight markers in kb are shown on the left.

FIG. 3 illustrates construction of a SXT sensitive derivative of O139 vaccine strain Bengal-2 by allele exchange using p442.$SXT^S$. A possible recombination of p442.$SXT^S$ with the SXT element in the Bengal-2 chromosome (through the homology in the light gray areas) is depicted as the cointegrate. Molecular weight markers in kb are shown on the left.

FIG. 4 shows southern blot analysis of the SXT element and the genes encoding and flanking the O139 serogroup antigen in *V. cholerae* O139 strains MO10 and E712, *V. cholerae* O1 strain C6709, and cosmids pSXT1 and pO139-1. The cosmid and chromosomal DNA was purified, digested with EcoRI and analyzed by Southern blot hybridization first using pSXT1 (left) and subsequently after stripping, pO139-1 (right) as probes. EcoRI sites flank the inserts in the cosmids allowing the 'vector' band to be identified. Molecular weight markers in kb are shown on the left.

FIG. 5 shows southern blot analysis of the hybridization of a large internal fragment of the SXT element (pSXT1) with SXT resistant O139 strain MO10 (a 1992 isolate from India), O1 strains CO-941, CO-966, CO-968, CO-970 (1994 isolates from India), and F1873 and F1875 (1994 isolates from Zaire) and cosmid pSXT1. The fragments labeled 'E' refer to sequences within the SXT element, and the fragment labeled 'V+E' refers to 'vector' related plus 'element' related sequences in pSXT1. Molecular weight markers in kb are shown on the left.

DESCRIPTION OF THE PREFERRED EMBODIMENTS

Bengal 0139, a cholera strain which has caused severe epidemics is resistant to multiple common antibiotics.

We have shown that the O139 serogroup antigen of the Bengal 0139 *V. cholerae* strain consists of both capsular and LPS determinants and is encoded by genes that are not present in El Tor O1 strains. This led us to conclude that the evolution of *V. cholerae* O139 from an El Tor O1 strain must have involved horizontal gene transfer of the O139 antigen encoding genes from a donor strain followed by recombination of these genes with the El Tor O1 chromosome. To continue to address the question of how an El Tor O1 strain may have given rise to *V. cholerae* O139, we have investigated the genes which encode the antibiotic resistances which are characteristic of the O139 serogroup. Our results indicate that the characteristic antibiotic resistances in Bengal 0139 are part of a much larger, novel genetic element with properties similar to a conjugative transposon. This element may be removed or disrupted to make a *V. cholerae* vaccine or heterologous antigen vector which has enhanced safety by virtue of its sensitivity to commonly used antibiotics.

In the current study, we found that 4 of 5 antibiotic resistances characteristic of *V. cholerae* O139 (sulfamethoxazole, trimethoprim, chloramphenicol, and streptomycin) are carried on an approximately 62 kb self-transmissible, chromosomally-integrating genetic element which we have termed the SXT element. The conjugative range of this element included *E. coli* as well as *V. cholerae* O1 suggesting that the SXT element has a fairly broad host range. In both *V. cholerae* as well as *E. coli* the SXT element integrates into the chromosome by a site-specific mechanism that does not require recA.

The properties of the SXT element—large size, self-transmissibility, site-specific integration and linked antibiotic resistances, are similar to the conjugative transposons found in the Gram-negative obligate anaerobe Bacteroides. The SXT element appears to be the first example of a conjugative transposon in the proteobacteria. Also, to our knowledge, trimethoprim, sulfonamide, chloramphenicol, and streptomycin resistance have not previously been shown to be encoded by conjugative transposons.

Transferable resistance to trimethoprim in *V. cholerae* has been attributed to R factors. However, in some of these cases (Jesudason et al., Trans. Roy. Soc. Trop. Med. Hyg. 84:137–138, 1990; Matsushita et al., Microbiol. Immunol. 28:1159–1162, 1984) the presence of a plasmid encoding trimethoprim resistance was only inferred by the transmissibility of the antibiotic resistance.

The SXT element, unlike the Gram-positive conjugative transposons (Clewell et al., 1995, supra) apparently requires recA for the conjugal transfer of resistance to SXT. Deletion of recA from the O139 donor strain abolished its ability to transfer resistance to SXT, while deletion of recA from the recipient strain only diminished the frequency of acquisition of $SXT^R$. Presumably RecA function is required for the excision of the SXT element from the donor chromosome; however, the precise role that RecA plays in the transfer of the SXT element remains to be defined.

Many studies have suggested that an El Tor O1 strain of V. cholerae gave rise to V. cholerae O139. It now seems clear that the genes encoding the O139 serogroup antigen were transferred to an El Tor O1 strain and these genes subsequently recombined with the El Tor O1 chromosome to give rise to V. cholerae O139. Resistance to SXT and low level streptomycin is characteristic of V. cholerae O139. This close association of these antibiotic resistances with the new serogroup antigen suggests that either the El Tor O1 progenitor of V. cholerae O139 harbored the SXT element or that the SXT element and the genes encoding the O139 serogroup antigen were introduced at the same time into the El Tor O1 strain that gave rise to V. cholerae O139. If this co-inheritance of the SXT element and the genes encoding the O139 serogroup antigen did in fact occur, selective pressure to become resistant to SXT may have led to the emergence of the new V. cholerae serogroup. Our finding of the lack of close linkage of the genes encoding the O139 serogroup antigen and the genes encoding resistance to SXT decreases the likelihood that co-inheritance of these two gene clusters was a step in the genesis of O139. Certainly, the genes encoding the O139 serogroup antigen are not part of the SXT element. However, it is possible that the SXT element, like the Bacteroides conjugative transposons, is capable of mobilization of unlinked chromosomal gene clusters (elements termed NBUs in Bacteroides (Salyers et al., 1995, supra)). If the genes encoding the O139 serogroup antigen are part of an NBU-like element, then it is conceivable that the SXT element may have mobilized these genes (along with itself) from a donor chromosome into an El Tor recipient strain to give rise to V. cholerae O139 in essentially a single step.

The El Tor O1 strains which have re-emerged after the O139 epidemic contain a related but not identical self-transmissible $SXT^R$ encoding element. The current broad dissemination of these elements in V. cholerae O1 and V. cholerae O139 strains on the Indian subcontinent may suggest that these elements confer some selective advantage to V. cholerae. Although our results indicate that the SXT element does not encode an intestinal colonization factor, it is possible that the SXT element plays some other role in the virulence of V. cholerae or in its environmental ecology.

In the past decade, there have been significant strides made in the development of live-attenuated V. cholerae vaccine strains (Mekalanos et al., Science 265:1387–1389, 1994). Our group has constructed and tested live-attenuated O139 vaccine strains (U.S. Pat. No. 4,882,278; U.S. Pat. No. 5,330,753, which is a continuation of U.S. Ser. No. 07/188, 016, which is a continuation of U.S. Ser. No. 07/043,907 all of which are now abandoned; U.S. Ser. No. 08/367,115, filed Jan. 5, 1995, pending; U.S. Ser. No. 08/349,403, filed Dec. 2, 1994, abandoned, all of which are hereby incorporated by reference). Ideally, such vaccines should be not only safe for the individual vaccinee, but also should be incapable of disseminating deleterious genes encoding virulence factors or antibiotic resistances to other organisms in the environment (Mekalanos, Current Opinion in Biotechnology 5:312–319, 1994). Our finding that the genes encoding resistance to SXT are part of a self-transmissible element in V. cholerae O139 indicate that V. cholerae O139 vaccine strains may be improved by the elimination of their SXT element or the resistance genes it encodes. In this regard, we have shown that it is possible to introduce a large internal deletion of the SXT element and thus render the vaccine strain Bengal-2 sensitive to SXT. The resultant strain, Bengal-2.$SXT^S$ effectively colonizes the infant mouse small intestine, suggesting that this strain, like our previous O139 vaccine candidates (Coster et al., 1995, supra) will be an effective immunogen (Herrington et al., J. Exp. Med. 168:1487–1492, 1988). To further ensure this vaccine's genetic stability, environmental safety and lack of reactogenicity, one can introduce a recA deletion and a mutation abolishing motility according to the cholera vaccine "blueprint" that we have recently outlined (see U.S. patent applications incorporated by reference, supra).

The following examples are meant to illustrate, not limit, the invention.

Materials and Methods

Bacterial Strains, Media and Antibiotic Susceptibilites

The bacterial strains and plasmids used in this study are described in Table 1. Bacterial strains were maintained at −70° in Luria Bertani (LB) broth (Miller, Cold Spring Harbor Laboratory Press, N.Y., 1992) containing 20% (vol/vol) glycerol. Bacterial strains were tested for susceptibilities to furazolidone (100 $\mu$g), streptomycin (10 $\mu$g), streptomycin (50 $\mu$g), sulfisoxazole (0.25 mg), trimethoprim (5 $\mu$g), and sulfamethoxazole 23.75 ($\mu$g)-trimethoprim (1.25 $\mu$g) by the disk diffusion technique as described and chloramphenicol (1.5 $\mu$g) (Nat'l.

Committee for Clinical Laboratory Standards, 4th ed., vol. 10, NCCLS, Villanova, Pa., 1990). The standardized zone size criteria used for the interpretation of antibiotic susceptibilites for the Enterobacteriaceae (Nat'l. Committee for Clinical Laboratory Standards, 1990, supra) were used for the Vibrio cholerae strains because these interpretive criteria have not been established for V. cholerae.

Bacterial Conjugations

Conjugation experiments were carried out on LB plates. In the matings between V. cholerae strains, a donor strain, usually the O139 strain MO10, resistant to sulfamethoxazole and trimethoprim ($SXT^R$) and sensitive to kanamycin (Km) was streaked together with an SXT sensitive ($SXT^S$) recipient strain marked with Km. In matings between $SXT^R$ V. cholerae strains and E. coli recipients, the recipients were marked with either tetracycline or rifampicin. These plate matings were carried out overnight at 37° with a donor to recipient ratio of approximately 1:1. The next day, the cells were scraped off the mating plates and transferred to LB agar plates containing trimethoprim (32 $\mu$g/ml) and sulfamethoxazole (160 $\mu$g/mL) to select against unmated recipients and kanamycin (60 $\mu$g/ml) or tetracycline (15 $\mu$g/ml) or rifampicin (50 $\mu$g/ml) to select against the donor. The frequency of transfer of resistance to SXT to recipient cells was quantified by recovering the mating mixtures off of the LB plates into LB broth and then plating dilutions of the recovered cells on selective media. The frequency of conjugation was determined by dividing the number of $SXT^R$ recipient cells by the total number of recipient cells. Molecular methods. Plasmid DNA was prepared by Qiagen column and chromosomal DNA was prepared using the Invitrogen Easy DNA kit according to the manufactures' instructions. For pulsed-field gel electrophoresis analyses, DNA samples were prepared, restriction enzyme digested, and electrophoresed in 1% agarose gels using previously described conditions (Prager et al., Med. Microbiol. Letters 5:219–217, 1994). Southern blotting using probes conjugated to horseradish peroxidase to enable hybridization to be detected with a chemiluminescent substrate (Amersham) was performed as previously described (Waldor et al., 1994, sura).

Construction of the O139 Cosmid Library and Isolation of Cosmids Encoding Resistance to SXT and the O139 Serogroup Antigen The cosmid vector SuperCos 1 (Stratagene) was used to construct a cosmid library of Sau3AI partially digested DNA isolated from the O139 strain MO10. The *E. coli* strain XLI-Blue MR (Stratagene) was transfected with the ligated and packaged cosmids. Cosmids encoding resistance to SXT were identified by plating XLI-Blue MR strains containing the cosmid library on LB agar plates containing trimethoprim (32 μg/ml) and sulfamethoxazole (160 μg/mL). One of these cosmids encoding resistance to SXT, designated pSXT1, was used for most of the subsequent analyses of the mobile genetic element that included the genes encoding resistance to SXT. To isolate a cosmid carrying genes involved in the synthesis of the O139 serogroup antigen, the library (in XLI-Blue MR) was screened by hybridization with the O139-specific gene probes 2R1 and 2R3 (Nair et al., J. Clin. Microbiol. 33:2186–2187, 1995; Waldor et al., Lancet 343:1366, 1994). One cosmid identified in this way, pO1391-1, was found to complement Bengal-2R1, an O139-derivative of the O139+strain Bengal-2 (Waldor et al., Proc. Nat'l. Acad. Sci. USA 91:11388–11392, 1994), which contains a Tn5lac insertion in a gene required for O139 antigen biosynthesis.

Construction of an $SXT^S$ derivative of the O139 vaccine strain Bengal-2.

Figure 3:
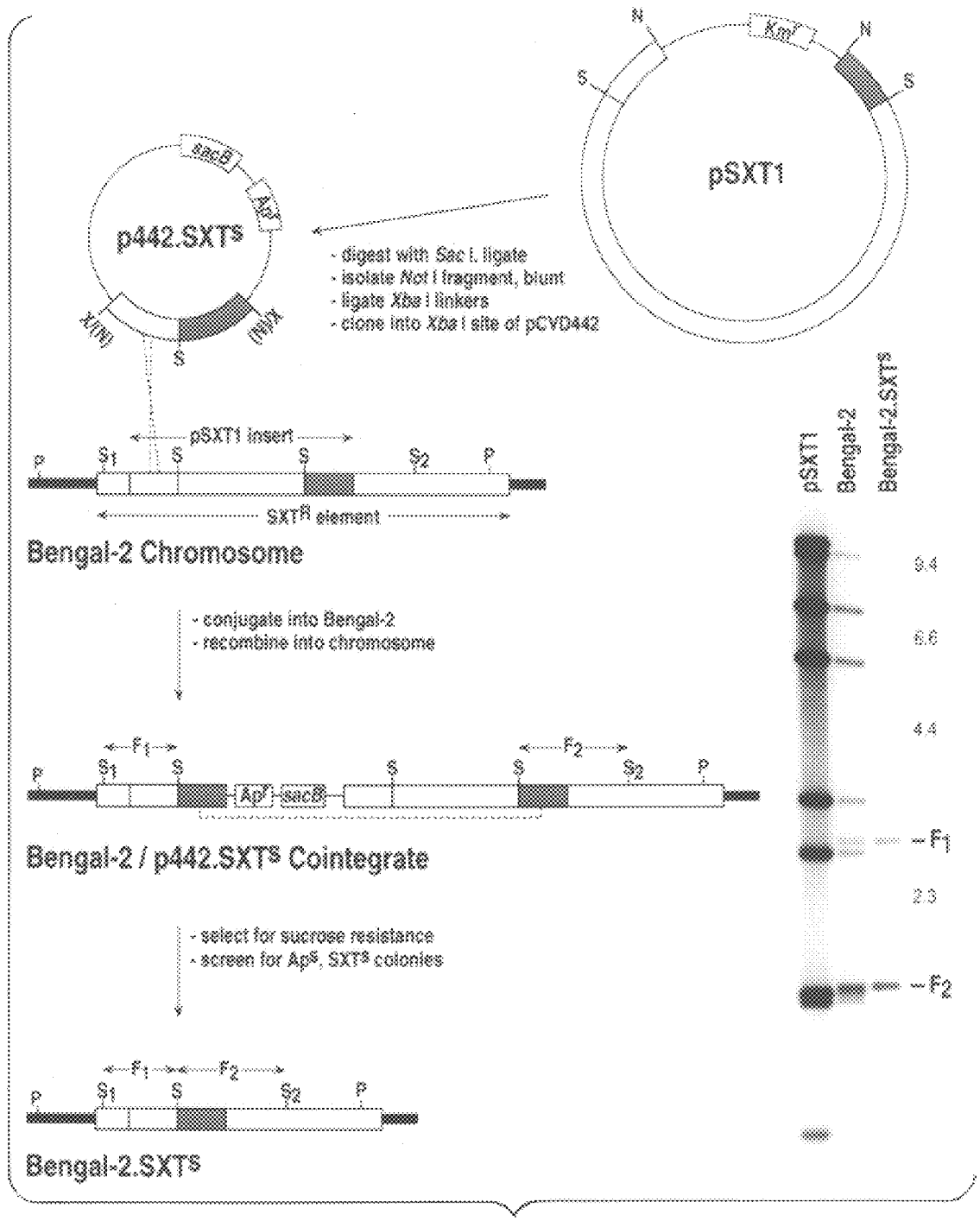

Allelic exchange was used to delete genes involved in resistance to SXT from Bengal-2, a live attenuated vaccine derivative of strain MO10 which contains a deletion of the entire CTX genetic element and high level streptomycin resistance as an environmental marker (Waldor et al., 1994, supra). The allelic exchange vector p442.$SXT^S$ was constructed as schematically shown in FIG. 3. First, a large internal deletion in the insert in pSXT1 was identified by digesting pSXT1 with SacI, an enzyme which does not cut within the cosmid vector (SuperCos I); the products of this digestion were ligated, and used to transform XLI Blue MR using kanamycin (the marker carried by the cosmid vector) as a selection to identify plasmid pSXT$^S$.ΔSac1. This plasmid contains a 34.5 kb internal deletion in pSXT1 and no longer confers resistance to SXT or low level streptomycin (Table 2). Second, the insert in pSXT$^S$.ΔSacI was cut out of the vector using NotI; blunt ends were generated with T4 polymerase and then XbaI linkers were added; following digestion with XbaI and gel purification, this insert was ligated with XbaI digested and phosphatased pCVD442 (Donnenberg et al., Infect. Immun. 59:4310–4317, 1991). Third, the ligation reaction was used to transform *E. coli* strain SM10λpir (Miller et al., J. Bacteriol. 170:2575–2583, 1988) for ampicillin resistance yielding the recombinant plasmid p442.$SXT^S$. Plasmid p442.$SXT^S$ was then mobilized from Sm10λpir into Bengal-2 by conjugation using streptomycin (150 μg/ml) and ampicillin (80 μg/ml) to identify integrations of p442.$SXT^S$ into the Bengal-2 chromosome. These ampicillin resistant p442.$SXT^S$ integrant derivatives of Bengal-2 were then plated on LB agar plates containing no NaCl and 10% sucrose as described (Butterton et al., Infect. Immun. 63:2689–2696, 1995) to detect the allele exchange event giving rise to the ampicillin sensitive, sucrose resistant, SXT sensitive strain Bengal-2.$SXT^S$.

Mouse Colonization Assay

Colonization of the suckling CD-1 mouse small intestine was assessed by competition assays using approximately 1:1 mixtures of test strains as described (Waldor et al., 1994, supra). An in vitro competition in LB broth was done concomitantly with the same cell mixtures used to inoculate the suckling mice to assess the relative growth rates of the test strains in rich media. All the bacterial strains used in the competition assays were resistant to streptomycin and bacterial cells were recovered after the in vivo or in vitro competitions by plating on LB agar plates containing streptomycin (100 μg/ml). The fraction of $SXT^R$ cells recovered from the competitions was determined by replica plating.

The Genes Encoding Trimethoprim, Sulfamcthoxazole, Chloramphenicol, and Streptomycin Resistance are Physically Linked to a Self-Transmissible Genetic Element Clinical isolates of *V. cholerae* O139 are characteristically resistant to the antibiotics trimethoprim, sulfamethoxazole, streptomycin (low level) and furazolidone but are typically sensitive to tetracycline, ampicillin, chloramphenicol, erythromycin and ciprofloxacin (Albert et al., Lancet 341:704, 1993; Ramamurthy et al., Lancet 341:703–704, 1993). O139 strains are also resistant to the vibriostatic compound O/129 (Albert et al., 1993, supra) but this phenotype probably reflects a trimethoprim resistant dihydrofolate reductase (Gerbaud et al., 1985, supra). This pattern of antibiotic susceptibilities was not characteristic of the resident El Tor O1 strains which the O139 strains replaced (Albert et al., 1993, supra). To begin to characterize the genes which encode these antibiotic resistances in *V. cholerae* O139, we constructed a cosmid library from the O139 clinical isolate MO10, a strain isolated from Madras, India in late 1992 (Waldor et al., 1994, supra) which exhibits the antibiotic resistances that are characteristic of other O139 strains. A cosmid containing the genes encoding resistance to sulfamethoxazole and trimethoprim (SXT) was isolated from the library by plating the library on SXT. This cosmid, which contained a 38 kb insert was designated pSXT1. It also encoded low level resistance to streptomycin (Table 2) indicating that the *V. cholerae* O139 genes which encode resistance to SXT and streptomycin are linked. The cosmid did not confer resistance to furazolidone.

The finding that the genes encoding four of the antibiotic resistances characteristic of *V. cholerae* O139 were linked, suggested that this gene cluster might be transmissible as part of a plasmid or other genetic element. Conjugation experiments were undertaken to determine if this cluster of antibiotic resistance genes was self-transmissible to *V. cholerae* O1 recipient strains of either the El Tor or classical biotype. The O139 strain MO10 was mated on plates with either the $Km^R$ El Tor O1 strain E4 (Goldberg et al., J. Bacteriol. 165:723–31, 1986) or the $Km^R$ classical O1 strain O395-NT (Mekalanos et al., Nature 306:551–7, 1983). $SXT^R$ recipient E4 colonies were found at a frequency of $2 \times 10^{-7}$ and $SXT^R$ O395-NT colonies were found at a frequency of $3 \times 10^{-9}$. The $Km^R$, $SXT^R$ colonies retained the O1 serogroup antigen indicating that they were indeed transconjugates rather than spontaneous $Km^R$ mutants of the O139 donor strain MO10.

The $SXT^R$ *V. cholerae* O1 transconjugates were in turn capable of conjugal transfer of resistance to SXT to other *V. cholerae* O1 strains and to *E. coli* K12 derivative strains (see below) indicating that all of the genes required for transmission of resistance to SXT were transferred in the conjugation events. The *V. cholerae* transconjugates were not resistant to furazolidone indicating that the gene(s) encoding resistance to this antibiotic are not part of the same self-transmissible "SXT element" (Table 2). However, subsequent conjugation experiments revealed that resistance to streptomycin was in fact co-transferred with resistance to sulfamethoxazole and trimethoprim (Table 2) indicating that all three of these antibiotic resistance determinants are part of the same self-transmissible SXT element.

The self-transmissible nature of the SXT element suggested that it might be a plasmid or R factor. However, several different types of plasmid preparation procedures performed on donor strain MO10 failed to reveal detectable plasmid DNA. Pulsed-field gel electrophoresis was used to investigate whether the SXT element was integrated into the chromosome of the $SXT^R$ *V. cholerae* O1 transconjugates. The ethidium stained pulsed-field gel of SfiI digested total DNA preparations from E4 and E4-$SXT^R$-1 showed that the acquisition of the SXT element by strain E4 led to the loss of a band (labeled A in FIG. 1) and the acquisition of 3 new bands (labeled N1, N2, and N3 in FIG. 1). This establishes that the SXT element integrated into the chromosome of the recipient strain. The size of the element, estimated by adding together the sizes of the three novel bands, N1, N2, and N3 (270 kb, 220 kb, and 12 kb respectively) and subtracting the size of the lost band A (440 kb), is approximately 62 kb.

Figure 2:
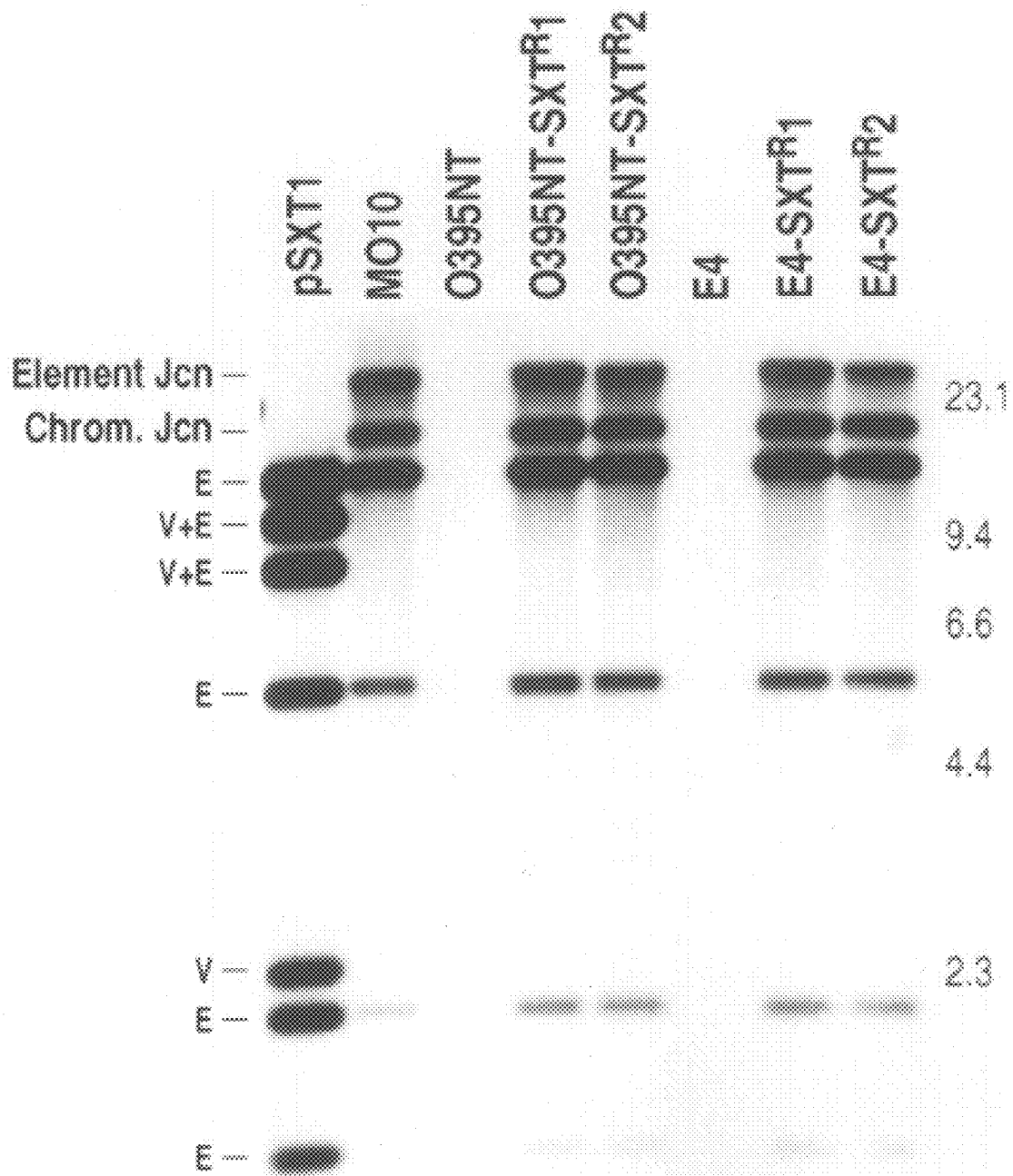

Southern blot analyses of the $SXT^R$ O1 transconjugates were performed using the entire cosmid pSXT1 as a probe. This large probe hybridized only to the O139 donor strain MO10 and the $SXT^R$ O1 transconjugates but not to the *V. cholerae* O1 strains (FIG. 2). Thus the SXT element includes all of the 38 kb insert of pSXT1 and this insert contains no *V. cholerae* O1 DNA. The restriction fragments which hybridized to the pSXT1 probe in the transconjugates included 4 fragments which are also within the insert in pSXT1 (the bands labeled 'E' in FIG. 2) and two additional junction fragments that extend into the SXT element sequences that have not been cloned in pSXT1. Other restriction digests revealed that one of these junctions is with the O1 chromosome and the other junction lies within the SXT element itself. The independently-derived *V. cholerae* O1 $SXT^R$ transconjugates showed the same sized chromosomal junction fragment (FIG. 2) suggesting that in *V. cholerae* the SXT element inserts into the recipient chromosome with insertion site-specificity.

The conjugative range of the SXT element was not limited to *V. cholerae*. MO10 was able to donate the SXT element to a variety of *E. coli* strains including MM128 (Ferro-Novick et al., Cell 38:211–217, 1984) and CV601 (Tschape et al., J. Gen. Micro. 127:155–160) at frequencies at least one log greater ($6 \times 10^{-6}$) than the frequency of transmission of the element to the *V. cholerae* strain E4. Like the $SXT^R$ *V. cholerae* O1 transconjugates, the $SXT^R$ *E. coli* transconjugates were capable of transferring resistance to SXT to $SXT^S$ *E. coli* or *V. cholerae* recipients. The *E. coli* recipients of the SXT element became resistant to streptomycin along with sulfamethoxazole and trimethoprim demonstrating that the genes encoding the resistance to each of these antibiotics are part of the self-transmissible SXT element (Table 2). Pulsed-field gel electrophoresis of SfiI digested DNA prepared from three independently derived *E. coli* $SXT^R$ transconjugates showed the loss of the same sized restriction fragment (labeled 'B' in FIG. 1) in these transconjugates, suggesting that the SXT element inserts into a preferred chromosomal SfiI fragment in the recipient *E. coli* cells.

The data presented above suggested that the SXT element was a self-transmissible, site-specific transposon similar in properties to the conjugative transposons described in Gram-positive cocci and Bacteroides (Clewell et al., 1995, supra; Salyers et al., 1995, supra). Because most transposons can integrate into target DNA in a recA independent fashion we tested the effect of recA deletion on the integration of the SXT element. Inactivation of recA in the *E. coli* recipients or recA deletion in the *V. cholerae* recipients decreased the frequency of transmission of the SXT element from MO10 to *E. coli* or *V. cholerae* by approximately 20–50 fold (not shown). However, inactivation or deletion of recA in either the recipient *E. coli* or *V. cholerae* strains did not influence the site of insertion of the SXT element. This suggests that the site-specific integration of the SXT element is largely independent of recA-mediated homologous recombination.

Construction of an $SXT^S$ O139 Vaccine Strain: Evidence that the SXT Element Does not Encode an Intestinal Colonization Factor The large size of the SXT element suggests it may encode a variety of other properties besides antibiotic resistances. The rapid dissemination of *V. cholerae* O139 on the India subcontinent and its initial rapid replacement of the endemic El Tor O1 strains raised the possibility that the SXT element might encode virulence factors. To begin to address this possibility, we constructed an O139 strain with a large internal deletion in the SXT element. We undertook this construction in strain Bengal-2, a vaccine derivative of strain MO10 which contains a deletion of the entire CTX genetic element (Waldor et al., 1994, supra). Although a derivative of this vaccine prototype appears safe and effective in early human trials (Coster et al., 1995, supra), this vaccine, as well as another live O139 vaccine construct (Tacket et al., 1995, supra) retain the antibiotic resistances that are characteristic of most O139 clinical isolates. Thus in an effort to improve the safety of our O139 vaccine strain we deleted the genes encoding resistance to SXT together with much of the DNA flanking these antibiotic resistances in the SXT element from the chromosome of O139 vaccine strain Bengal-2 (see Methods, supra, and FIG. 3). The resultant strain, Bengal-2.$SXT^S$ carries a 34.5 kb internal deletion in the SXT element.

Evidence that the SXT Element Does not encode an intestinal colonization factor

Colonization of the small intestine is a critical step in the pathogenesis of cholera and a variety of gene products are known to facilitate the colonization process. We therefore tested whether the large 34.5 kb deletion introduced into Bengal-2 to generate Bengal-2.$SXT^S$ altered the strain's capacity to colonize the small intestine of the suckling mouse. To study the colonization properties of Bengal-2.$SXT^S$, competition assays were performed in which mixtures of Bengal-2 ($SXT^R$) and Bengal-2.$SXT^S$ ($SXT^S$) were inoculated in vivo into suckling CD-1 mice or in vitro into LB broth. There was no significant change in the ratio of $SXT^R$ cells to $SXT^S$ cells after the 21 hours of either in vivo or in vitro growth (Table 3). Therefore, the deletion in Bengal-2.$SXT^S$ has not compromised its capacity to colonize the suckling mouse small intestine.

It remained possible that portions of the SXT element not deleted in strain Bengal-2.$SXT^S$ were important in virulence. To begin to address this possibility, we tested whether the El Tor or classical *V. cholerae* O1 $SXT^R$ recipients of the SXT element exhibited changes in their colonization of the suckling mouse small intestine. We performed competition assays between the $SXT^S$ parental strains E4 and O395-NT and their $SXT^R$ derivatives which had gained the SXT element after conjugation with MO10, (E4-$SXT^R$-1 and O395-NT-$SXT^R$- respectively).

One-to-one mixtures of the strain pairs E4 and E4-$SXT^R$-1 and O395-NT and O395-NT-$SXT^R$-1 were inoculated in vivo or in vitro and after 21 hours of growth approximately equal ratios of SXT$^S$ to SXT$^R$ colonies were recovered (Table 3). Thus it appears that insertion of the SXT element into either the E4 or O395-NT chromosome does not enhance or attenuate these strains' colonization capacities. Therefore, as assessed by the suckling mouse colonization assay, the SXT element does not appear to encode a colonization factor.

The Genes Encoding the O139 Serogroup Antigen are not Closely Linked to the SXT Element in *V. cholerae* O139

Figure 4:
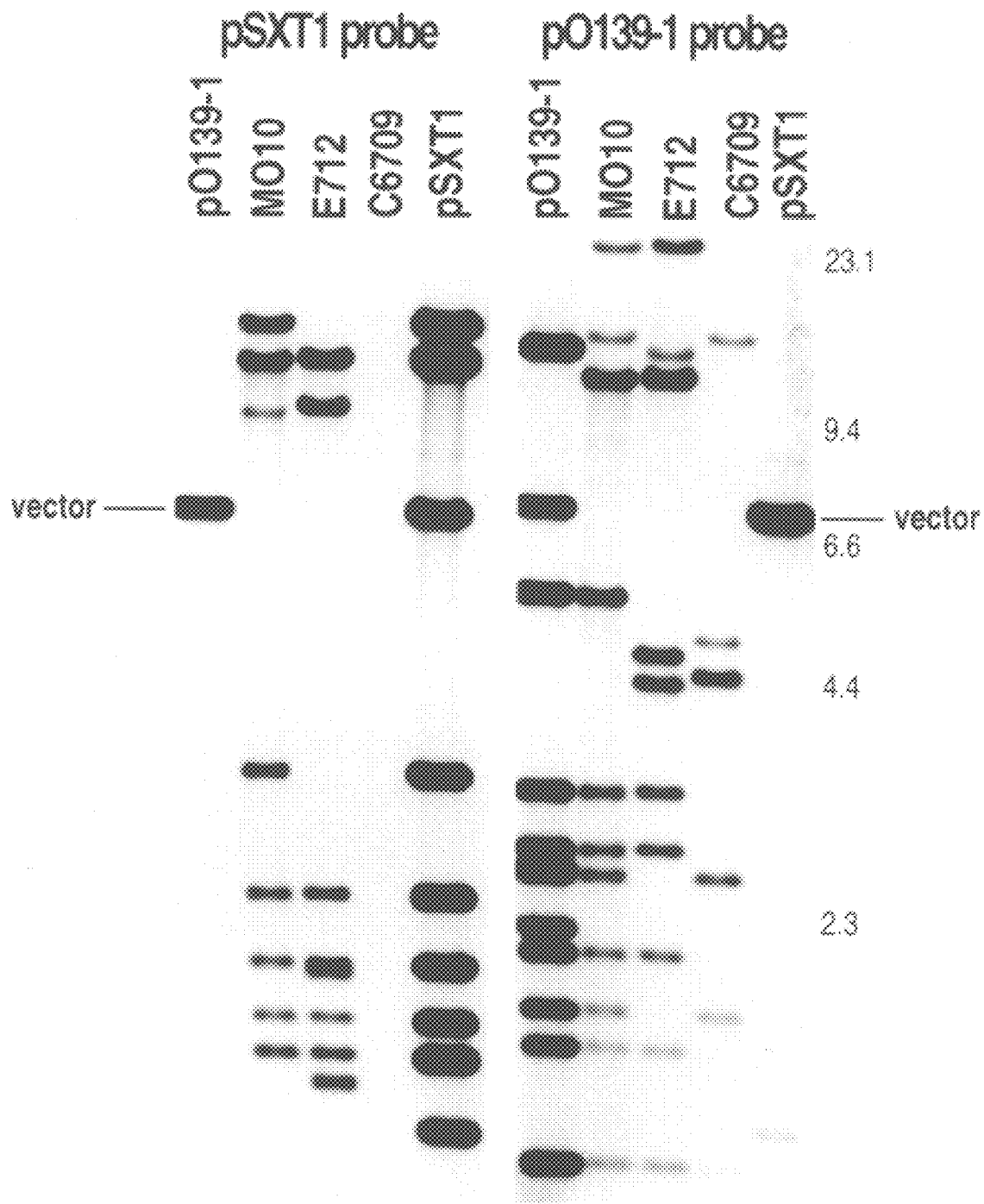

The selective pressures that led to the emergence of *V. cholerae* O139 from an endemic El Tor O1 strain on the Indian subcontinent are not established. Certainly the selective pressure of the immunity of the endemic population to *V. cholerae* O1, which is principally targeted at the O1 serogroup antigen, may have contributed to the emergence of this novel serogroup of *V. cholerae*. Also, if the SXT element included the genes which encode the O139 serogroup antigen, or if the SXT element can facilitate the conjugal transfer of linked genes, then the widespread use of SXT, a very popular and useful antibiotic combination, may have provided an additional selective pressure for the emergence of the new *V. cholerae* serogroup. To explore this possibility, we tested whether the SXT element was closely linked on the *V. cholerae* O139 chromosome to the genes which encode the O139 serogroup antigen. To test this possible linkage, a cosmid clone was isolated which can complement strain Bengal-2R1 (Waldor et al., 1994, supra), an O139 Tn5lac derivative of the O139$^+$ strain Bengal-2. This cosmid, pO139, was identified by probing the O139 cosmid library with our previously described O139 specific gene probes (Nair et al., 1995, supra; Waldor et al., 1994, supra). Southern blotting showed that the cosmids pSXT1, which encodes much of the SXT$^R$ element and pO139-1 which encodes the O139 serogroup antigen only share a common vector band and do not have any cross-hybridizing restriction fragments (FIG. 4). When these cosmids were used as probes of EcoRI digested MO10 DNA, they did not hybridize with any of the same chromosomal fragments (FIG. 4). Also, cosmids which overlap with pSXT1 and also encode SXT$^R$ did not hybridize with pO139-1 (not shown). Finally, there were no cross-hybridizing restriction fragments when pulsed-field gels of SfiI digested DNA from O139 strains was sequentially probed with pO139-1 and pSXT1 (not shown). These data suggest that the SXT element is not closely linked (i.e., within approximately 40 kb) to the genes encoding the O139 serogroup antigen.

Strain E712 has been proposed as a potential donor for the genes encoding the O139 serogroup antigen (Prager et al., 1994, supra). E712 certainly has characteristics that suggest it maybe a potential O139 donor strain. It is serologically O139+butlike most non-O1, non-O139 strains, it is genotypically ctxAB$^-$ (Prager et al., 1994, supra) and tcpA- (not shown). When the cosmid pO139 was used to probe Southern blots of restriction digests of E712 and MO10 DNA, there were many shared restriction fragments (FIG. 4), however, there were also differences suggesting that E712 was probably not the donor for the genes encoding the O139 serogroup antigen. It is interesting to note however, that E712, like other O139$^+$ strains is resistant to SXT and low level streptomycin. Like MO10, strain E712 was able to transfer resistance to SXT to both *V. cholerae* O1 and to *E. coli* recipient strains in plate matings. However, the SXT$^R$ recipient strains in these conjugation experiments, regardless of whether E712 or MO10 was the donor, did not become serologically O139$^+$. These data suggest that the transfer of the SXT element does not generally lead to the acquisition of the O139 serogroup antigen.

Dissemination of the SXT$^R$ Element

Figure 5:
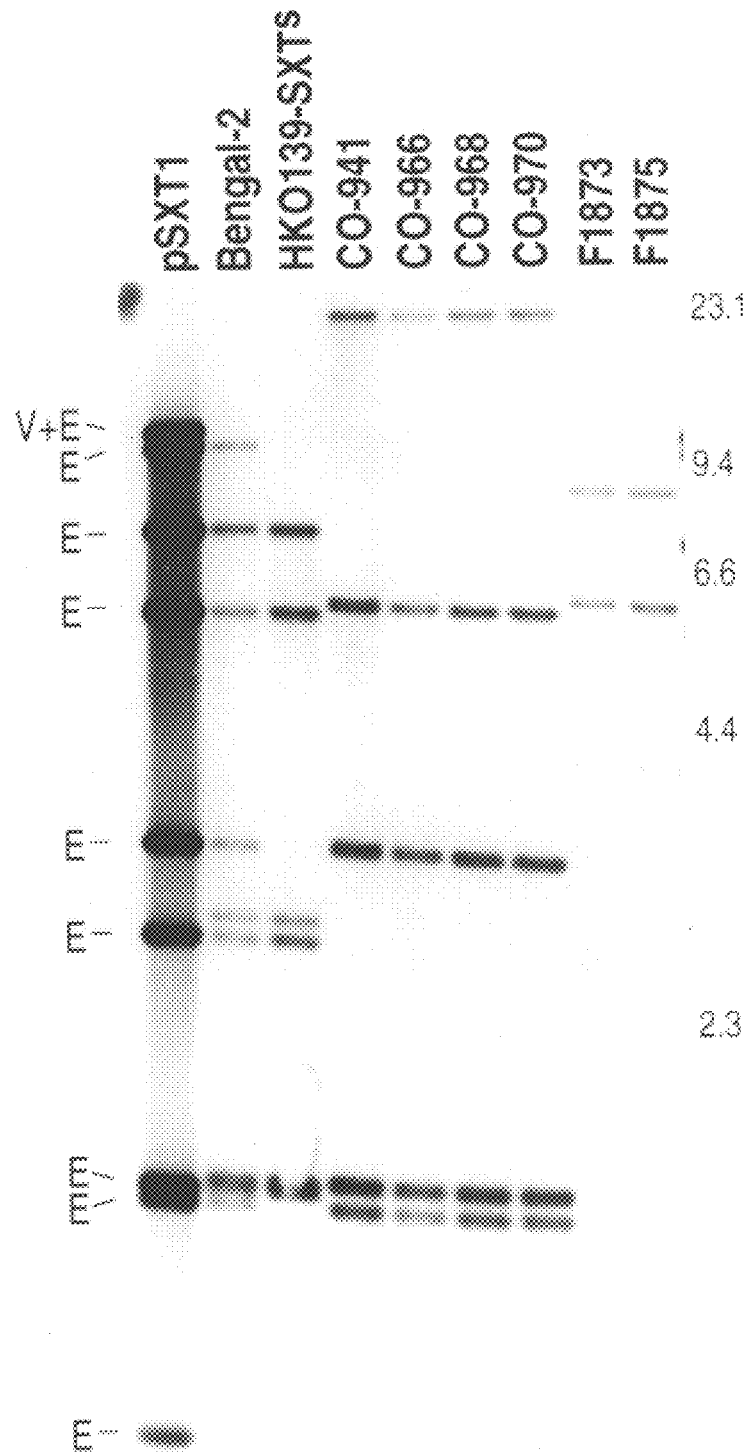

In late 1992 and early 1993 when *V. cholerae* O139 emerged on the Indian subcontinent, this new serogroup largely replaced the endemic El Tor O1 strains from most of the Indian subcontinent (Nair et al., J. Infect. Dis. 169:1029–34, 1994). However, in the past 2 years, El Tor O1 *V. cholerae* strains have returned to the Indian subcontinent and most recently El Tor O1 strains are in fact the predominant cause of cholera in Bangladesh (Cholera Working Group, 1994, supra). The El Tor O1 strains which re-emerged in India and Bangladesh after the explosive O139 epidemic were reported to be resistant to sulfamethoxazole, trimethoprim and streptomycin (Yamamoto et al., 30th Joint Conference U.S.-Japan Cooperative Medical Science Program, Fukuoka, Japan, 1994). This raised the possibility that the wide dissemination of *V. cholerae* O139 led to the dissemination of the SXT element to these newly re-emerged El Tor O1 strains. We tested whether clinical isolates of these recent SXT$^R$ El Tor O1 strains contained the SXT element by Southern blot analysis with pSXTI as the probe. Compared with the O139 strain MO10, there was a substantial amount of hybridization of pSXT1 to 4 recent SXT$^R$ El Tor O1 strains from India (FIG. 5, strains CO-941, CO-966, CO-968, and CO-970) but, there were significant differences in the hybridization patterns in these 4 strains compared to MO10 (FIG. 5). In conjugation experiments, these new Indian SXT$^R$ El Tor O1 strains were able to transfer resistance to SXT to the SXT$^S$ El Tor O1 strain E4 suggesting that self-transmissible genetic elements are actually widely disseminated in *V. cholerae*. Although O139 strains and the newly emerged Indian El Tor O1 strains contain self-transmissible SXT resistance, the restriction site polymorphisms suggest that these elements are not identical. Thus the El Tor O1 strain which was the progenitor of *V. cholerae* O139 was probably not derived from one of these recent SXT$^R$ El Tor O1 strains. Rather, the SXT$^R$ El Tor O1 isolates that rebounded after the O139 epidemic may be representative of the SXT$^R$ El Tor O1 strains which were increasing in frequency in Southern India in the years prior to the O139 epidemic element (Nair et al., 1994, supra; Ramamurthy et al. 30:742–743, 1992). Furthermore, the SXT sensitive O139 strain HKO139-SXT$^S$ (Yam et al., Lancet 344:404–405, 1994) is not likely to be the progenitor of the epidemic O139 strain since Southern analysis revealed that this strain contains an internal deletion of part of the SXT element (FIG. 5).

TABLE 1

BACTERIAL STRAINS AND PLASMIDS USED IN THIS STUDY

| Strains and Plasmids | Description | Reference |
| --- | --- | --- |
| *V. cholerae* O139 | | |
| MO10 | Toxigenic 1992 clinical isolate from India | 42 |
| Bengal-2 | MO10 with deletion of CTX element; high level streptomycin resistance | 41 |
| Bengal-2.SXT$^S$ | Bengal-2 with internal deletion of SXT element | this study |
| E712 | non-toxigenic O139 isolate | 32 |
| *V. cholerae* O1 | | |
| O395-NT | classical strain; ΔctxAB::kan | 23 |
| O395-NT-SXT$^R$-1 | SXT resistant transconjugate of MO10 × O395-NT | this study |
| E4 | El Tor strain; ΔctxABN4, Km$^r$ | 13 |
| E4-SXT$^R$-1 | SXT resistant transconjugate of MO10 × E4 | this study |

TABLE 1-continued

BACTERIAL STRAINS AND PLASMIDS USED IN THIS STUDY

| Strains and Plasmids | Description | Reference |
|---|---|---|
| CO-941 | E1 Tor 1994 clinical isolate from India | this study |
| CO-966 | E1 Tor 1994 clinical isolate from India | this study |
| CO-968 | E1 Tor 1994 clinical isolate from India | this study |
| CO-970 | E1 Tor 1994 clinical isolate from India | this study |
| F1873 | E1 Tor 1994 clinical isolate from Goma, Zaire | this study |
| F1875 | E1 Tor 1994 clinical isolate from Goma, Zaire | this study |
| *E. coli* | | |
| MM128 | araD139 Δ(argF-lac) U169 rpsL150 re1A1 flB5301 deoC1 ptsF25 rbsR argG::Tn10 | 11 |
| MM128-SXT$^R$-1 | SXT resistant transconjugate of MO10 × MM128 | this study |
| CV601 | e14-(mcrA-)supE44 thi-1 thr-1 leuB6 lacY1 tonA21 Rif | 39 |
| SM10λpir | thi thr leu tonA lacY supE recA::RP4-2-Tc::Mu Km λpir | 26 |
| XL1-Blue MR | Δ(mcrA) 183Δ(mcrCB-hsdSMR-mrr) 173 endA1 supE44 thi-1 recA1 gyrA96 relA1 lac | stratagene |
| Plasmids | | |
| pSuperCosI | Cosmid cloning vector Ap Km | Stratagene |
| pSXT1 | pSuperCosI containing 38 kb insert encoding SXT, Sm | this study |
| pSXT$^S$.ΔSacI | pSXT1 with 34.5 kb deletion which removes SXT, Sm | this study |
| p0139-1 | pSuperCos1 containing 38 kb insert encoding 0139 antigen | this study |

TABLE 2

ANTIBIOTIC SUSCEPTIBILITIES OF STAINS BY DISK DIFFUSION METHOD

| | Antibiotic Susceptibilities | | | |
|---|---|---|---|---|
| Strain | Tmp$^a$ | Sulfa$^b$ | Sm$^c$ | Furaz$^d$ |
| *V. cholerae* 0139 | | | | |
| MO10 | R | R | R | R |
| Bengal-2 | R | R | R | S |
| Bengal-2.SXT$^S$ | S | S | S | S |
| E712 | R | R | R | R |
| *V. cholerae* 01 | | | | |
| 0395-NT | S | S | R | S |
| 0395-NT-SXT$^R$-1 | R | R | R | S |
| E4 | S | S | R | S |
| E4-SXT$^R$-1 | R | R | R | S |
| CO-941 | R | R | R | R |
| CO-966 | R | R | R | R |
| CO-968 | R | R | R | R |
| CO-970 | R | R | R | R |
| F1873 | R | R | R | S |
| F1875 | R | R | R | S |
| *E. coli* | | | | |
| XLI-Blue MR (pSuperCosI) | S | S | S | S |
| XLI-Blue MR-SXT1) | R | R | R | S |
| XLI-Blue MR (pSXT$^S$.ΔSacI) | S | S | S | S |
| XLI-Blue MR (p0139-1) | S | S | S | S |
| MM128 | S | S | R | N.D.$^e$ |
| MM128-SXT$^R$-1 | R | R | R | N.D. |

TABLE 2-continued

ANTIBIOTIC SUSCEPTIBILITIES OF STAINS BY DISK DIFFUSION METHOD

| | Antibiotic Susceptibilities | | | |
|---|---|---|---|---|
| Strain | Tmp$^a$ | Sulfa$^b$ | Sm$^c$ | Furaz$^d$ |
| CV601 | S | S | S | N.D. |
| CV601-SXT$^R$-1 | R | R | R | N.D. |

$^a$Trimethoprim 10 μg
$^b$Sulfisoxazole 0.25 μg
$^c$Streptomycin 10 μg
$^d$Furazolidone 100 μg
$^e$Not determined

TABLE 3

INTESTINAL COLONIZATION OF SXT$^R$ AND SXT$^S$ STRAINS

| Competing Strains | Inoculum (% SXT$^S$) *1 | In Vivo Competition Recovery (% SXT$^S$) *2 | In Vitro Competition Recovery (% SXT$^S$) |
|---|---|---|---|
| Bengal-2 alone | 0 | 0 | 0 |
| Bengal-2 Bengal-2.SXT$^S$ | 56 | 58 | 58 |
| 0395-NT-SXT$^R$-1 0395-NT | 51 | 48 | 46 |
| E4-SXT$^R$-1 E4 | 46 | 50 | 50 |

*1 Percentage of SXT$^S$ cells in the total number of cells in the inoculum.
*2 Median percentage of SXT$^S$ cells in the total number of cells recovered per group. There were at least 4 mice per group. There was no significant difference between the percentage of SXT$^S$ cells in the inoculum mixtures and in the cells recovered from the in vivo or in vitro competitions.

What is claimed is:

1. A genetically engineered *V. cholerae* cell, said engineered cell having sensitivity to an antibiotic selected from the group consisting of sulfamethoxazole, trimethoprim, chloramphenicol, and streptomycin, the parent of said engineered cell being resistant to said antibiotic.

2. The cell of claim 1, wherein said cell is a Bengal 0139 cell.

3. The cell of claim 1, wherein said sensitivity is the result of a deletion of a portion of the SXT genetic element.

4. The cell of claim 1, said cell being recA.

5. The cell of claim 1, wherein said sensitivity is to at least two of the antibiotics selected from the group consisting of sulfamethoxazole, trimethoprim, chloramphenicol, and streptomycin.

6. The cell of claim 5, wherein said sensitivity is to all of the antibiotics selected from group consisting of sulfamethoxazole, trimethoprim, chloramphenicol, and streptomycin.

7. A method of making a bacterial cell which is sensitive to at least one of the antibiotics selected from the group consisting of sulfamethoxazole, trimethoprim, chloramphenicol, and streptomycin, said method comprising the steps of:

a) taking a parental bacterial cell resistant to at least one of said antibiotics, said parental cell further comprising at least a portion of the SXT genetic element;

b) mutating said SXT genetic element; and c) screening for the sensitivity to at least one of said antibiotics to which the cell of step (a) was resistant.

8. The method of claim 7, said method further comprising a step of making said cell recap.

9. The method of claim 7, wherein said bacterial cell is *E. coli*.

10. The method of claim 7, wherein said parental bacterial cell is a *V. cholerae* cell.

11. The method of claim 10, wherein said *V. cholerae* cell is a non-01 *V. cholerae* cell.

12. The method of claim 11, wherein said non-01

UNITED STATES PATENT AND TRADEMARK OFFICE
CERTIFICATE OF CORRECTION

PATENT NO. 5,945,285
DATED August 31, 1999
INVENTORS John J. Mekalanos and Matthew K. Waldor It is certified that error appears in the above-identified patent and that said Letters Patent is hereby corrected as shown below:

On Cover Page

Other Publications - Col. 2, 7th reference, last line, change "91994" to --1994--.

In the Specification

Col. 2, line 10, after "well" insert --as--.

Col. 2, line 64, replace "and" with --an--.

Col. 3, line 3, replace "$10^{-18}$" with --$10^{-8}$--.

Col. 6, line 33, eliminate new paragraph indent and merge with prior paragraph.

Col. 7, line 5, replace "sura" with --supra--.

Col. 8, line 14, replace "Sulfamcthoxazole" with --Sulfamethoxazole--.

UNITED STATES PATENT AND TRADEMARK OFFICE
CERTIFICATE OF CORRECTION

PATENT NO. : 5,945,285
DATED : August 31, 1999
INVENTOR(S) : John J. Mekalanos and Matthew K. Waldor It is certified that error appears in the above-indentified patent and that said Letters Patent is hereby corrected as shown below:

Col. 8, line 60, eliminate new paragraph indent and merge with prior paragraph.

Col. 10, line 64, replace "0395-NT-SXT$^R$ - respectively" with --0395-NT-SXT$^R$-1 respectively--.

Col. 10, line 65, eliminate new paragraph indent and merge with prior paragraph.

Col. 11, line 28, replace "0139 Tn5lac" with --0139$^-$ Tn5lac--.

Col. 11, line 51, replace "0139+butlike" with --0139$^+$ but like--.

In the Claims

Col 15, line 2, replace "recap." with --recA--.

Signed and Sealed this

Seventeenth Day of April, 2001

Attest:

NICHOLAS P. GODICI

Attesting Officer          Acting Director of the United States Patent and Trademark Office